United States Patent
Bostian et al.

(10) Patent No.: US 6,322,973 B1
(45) Date of Patent: Nov. 27, 2001

(54) SURROGATE GENETICS TARGET CHARACTERIZATION METHOD

(75) Inventors: Keith Bostian, Menlo Park; Georges Natsoulis, San Francisco, both of CA (US)

(73) Assignee: Iconix Pharmaceuticals, Inc., Mountain View, CA (US)

( * ) Notice: Subject to any disclaimer, the term of this patent is extended or adjusted under 35 U.S.C. 154(b) by 0 days.

(21) Appl. No.: 09/187,918

(22) Filed: Nov. 6, 1998

Related U.S. Application Data

(60) Provisional application No. 60/064,897, filed on Nov. 7, 1997.

(51) Int. Cl.⁷ ............................... C12Q 1/68; C12Q 1/00; C12Q 1/70; C12N 15/09; C07H 21/04
(52) U.S. Cl. .................. 435/6; 435/4; 435/5; 435/29; 435/243; 435/69.1; 435/320.1; 435/325; 435/410; 435/455; 435/471; 536/23.1
(58) Field of Search ........................... 435/4, 5, 6, 29, 435/40.5, 243, 69.1, 325, 320.1, 410, 455, 471; 536/23.1

(56) References Cited

U.S. PATENT DOCUMENTS

| | | |
|---|---|---|
| 4,980,281 | 12/1990 | Housey . |
| 5,266,464 | 11/1993 | Housey . |
| 5,688,655 | 11/1997 | Housey . |
| 5,877,007 | 3/1999 | Housey . |
| 5,955,275 * | 9/1999 | Kamb ....................... 436/6 |
| 5,968,784 * | 10/1999 | Spinella et al. ............... 435/91.1 |

FOREIGN PATENT DOCUMENTS

| | | |
|---|---|---|
| 94/23039 | 10/1994 | (WO) . |
| 95/16694 | 6/1995 | (WO) . |
| 95/29254 | 11/1995 | (WO) . |
| 95/34680 | 12/1995 | (WO) . |
| 96/03499 | 2/1996 | (WO) . |
| 96/23075 | 8/1996 | (WO) . |
| 97/23642 | 7/1997 | (WO) . |
| 97/27213 | 7/1997 | (WO) . |
| 97/39119 | 10/1997 | (WO) . |
| 97/40170 | 10/1997 | (WO) . |
| 98/07886 | 2/1998 | (WO) . |
| 98/13514 | 4/1998 | (WO) . |
| 98/39483 | 9/1998 | (WO) . |

OTHER PUBLICATIONS

Fields et al., "The two–hybrid system: an assay for protein–protein interactions," *TIG*, 10(8):286–292 (1994).

Berendson, et al., "A Glimpse of the Holy Grail," *Science* 282:642–643 (1998).

Anderson et al., "Functional expression of a probable *Arabidopsis thaliana* potassium channel in *Saccharomyces cerevisiae*", *Proc. Natl. Acad. Sci. USA* 89:3736–3740 (1992).

Dasmahapatra et al., "A genetic system for studying the activity of a proteolytic enzyme," *Proc. Natl. Acad. Sci. USA* 89:4159–4162 (1992).

Ko et al., "TRK1 and TRK2 encode structurally related $K^+$ transporters in *Saccharomyces cerevisiae*," *Molecular and Cellular Biology* 11:4266–4273 (1991).

Kurtz et al., "Growth impairment resulting form expression of influenza virus M2 protein in *Saccharomyces cerevisiae*: Identification of a novel inhibitor of influenza virus," *Antimicrobial Agents and Chemotherapy* 39:2204–2209 (1995).

Lamb, "Do Vpu and Vpr of human immunodeficiency virus type 1 and NB of influenza B virus have ion channel activities in the viral life cycles," *Virology* 229:1–11 (1997).

Murray et al., "Inactivation of a yeast transactivator by the fused HIV–1 proteinase: A simple assay for inhibitors of the viral enzyme activity," *Gene* 134:123–128 (1993).

Smith et al., "Direct selection for sequences encoding proteases of known specificity," *Proc. Natl. Acad. Sci. USA* 88:5159–5162 (1991).

Tang et al., "Functional expression of a vertebrate inwardly rectifying $K^+$ channel in yeast," *Molecular Biol. Cell.* 6:1231–1240 (1995).

* cited by examiner

*Primary Examiner*—David Guzo
*Assistant Examiner*—Gerald G. Leffers, Jr.
(74) *Attorney, Agent, or Firm*—Robins & Pasternak LLP

(57) ABSTRACT

A two-step, scalable method is described for identifying the cellular function(s) of one or more genes of unknown function, and for identifying modulators of the gene(s). The method uses the reversal or alteration of a phenotype created by the expression of the heterologous gene, e.g., a human gene, to identify modulators of that gene's activity. That modulator is then used in an in vitro or in vivo disease model system to identify compounds which affect disease progression. The subset of compounds which influence disease in a therapeutic manner are drug leads. However, all compounds which influence disease progression are tools to at least partially characterize gene function. The inhibitor identification step of the method is preferably carried out using a plurality of microbial strains or cell lines expressing different heterologous DNA sequences in a single solution. The method is particularly useful for genes which have not been validated as good inhibitor targets.

5 Claims, 11 Drawing Sheets

| PROTEIN FAMILIES | MEMBERS | | PHENOTYPES IN YEAST OR E. COLI. |
|---|---|---|---|
| PROTEASES | | | |
| | RETROVIRAL PROTEASES | HTLV-1 | |
| | VIRAL PROTEASES | CYTOMEGLALOVIRUS | |
| | | HEPATITIS C | |
| | | EPSTEIN BARR | |
| | | HERPES-SIMPLEX | |
| | HUMAN PROTEASES | CASPASES | |
| | | ICE III | |
| | | ICE II | |
| | | ICE * | ? |
| | | ICE-LAPS | |
| | | ICH-1 | |
| | | Mch4 | |
| | | FLICE | |
| | | Mch2 | |
| | | CPP32* | ? |
| | | Mch3 | |
| | | METALLOPROTEINASES | |
| | | COLLAGENASES | |
| | | GELITINASES | |
| | | STROMELYSINS | |
| | | MT-MMPs | |
| | | MME | |
| | | MMP-18 | |
| | | MMP-19 | |

*FIG. 8A*

| PROTEIN | LOCALIZATION/BIOENESIS | SUBSTRATES | YEAST ASSAY | INHIBITOR |
|---|---|---|---|---|
| ICE FAMILY: | | | | |
| ICE | CYTOPLASMIC, HETERODERMIC, AUTOLYTIC CLEAVAGE OF ZYMOGEN | ASP/X, II, 1-B | GAL4 AUTOLYTIC EXCISION? | PEPTIDE-BAN BACULOVIRUS |
| ICErellI | AS ABOVE | ASP/X | | PEPTIDE-BAN |
| ICErellII | AS ABOVE | ASP/X | | BACULOVIRUS |
| CED3 FAMILY CPP32 | AS ABOVE | ASP/X, PARP | | PEPTIDE-BAN BACULOVIRUS COWPOX C |
| MCH3 | AS ABOVE | ASP/X | | PEPTIDE-BAN BACULOVIRUS |
| MCH2 | AS ABOVE | ASP/X | | PEPTIDE-BAN BACULOVIRUS |
| FLICE | AS ABOVE | ASP/X | | PEPTIDE-BAN BACULOVIRUS |
| MCH4 | AS ABOVE | ASP/X | | PEPTIDE-BAN BACULOVIRUS |
| ICH-1 | AS ABOVE | ASP/X | | PEPTIDE-BAN BACULOVIRUS |
| ICE-LAP6 | AS ABOVE | ASP/X | | PEPTIDE-BAN BACULOVIRUS |

FIG. 8B

| HUMAN MATRIX METALLOPROTEINASES (MMPs) |
|---|

GENERAL FEATURES NOT INCLUDED IN THE TABLE:

1. MMPs ARE INVOLVED IN NORMAL TISSUE REMODELING. MOST OF THEM MAY BE INVOLVED IN TUMOR INVASION AND METASTASIS, RHEUMATOID ARTHRITIS AND OTHER DISEASES RELATED TO MATRIX DEGRADATION.

2. BROAD-SPECTRUM INHIBITORS OF MMPs, MARITASTAT AND BATIMASTAT (BB94), HAVE BEEN DEVELOPED AND STUDIED IN CLINICAL TRIALS AND HAVE SHOWN PROMISING RESULTS IN COMBATING CANCER INVASION AND SPREAD (DETAILS NOT AVAILABLE).

3. A RECENT PAPER (1997. GENE. 190:55) STATED THAT YEAST PICHIA PASTORIS HAS INHERENT ABILITY TO CONVERT CLONED ZYMOGEN FORM OF MMPs INTO ACTIVE FORM, WHICH TEND TO SELF DEGRADE & SOMETIMES CAUSE CELL DAMAGE (NEED TO SEE THE PAPER)

| SUBCLASS | COMMON NAME | MMP-# | CAT DOMAIN (a.a., APPROX.) | CELLULAR LOCALIZATION | SUBSTRATE PROTEINS | INFO ON CLEAVAGE SITE SEQUENCES | EXPRESSION IN YEAST OR E. COLI. |
|---|---|---|---|---|---|---|---|
| COLLAGENASES | INTERSTITIAL COLLAGENASE | 1 | 163 | EXTRACELLULAR | COLLAGEN I, II, III; PROTEOGLYCAN, ETC. | CLEAVE COLLAGEN I, II, III INTO 3/4 & 1/4 LENGTH. THE SITES ARE KNOWN (JBC 272:2446) | |
| | COLLAGENASE 3 | 13 | 163 | EXTRACELLULAR | COLLAGEN I, II, III; PROTEOGLYCAN, ETC. | SEE MMP-1. ALSO CLEAVAGE SITES ON CARTILAGE AGGRECAN (FEBS LETT 380:17) | |
| | INTERSTITIAL COLLAGENASE | 8 | 163 | EXTRACELLULAR | COLLAGEN I, II, III, ETC. | SEE MMP-1. ALSO DIGEST AGGRECAN (SITE SEE J. CLIN. INV. 1996. 98:2292) | CAT DOMAIN IN E. COLI AS INCLUSION BODY; ACTIVE AFTER REFOLDING |

*FIG. 8C*

| SUBCLASS | COMMON NAME | MMP-# | CAT DOMAIN (a.a. APPROX.) | CELLULAR LOCALIZATION | SUBSTRATE PROTEINS | INFO ON CLEAVAGE SITE SEQUENCES | EXPRESSION IN YEAST OR E. COLI. |
|---|---|---|---|---|---|---|---|
| GELATINASES | GELATINASE A | 2 | 337, HAS A 19kD INSERT IN CAT DOMAIN | EXTRACELLULAR | GELATINS; LAMININS; COLLAGENS IV, V, VII, X; PROTEOGLYCAN | THE Ln-5 CLEAVAGE SITE KNOWN. COLLAGEN IV IS CUT INTO 170kD & 190kD FRAGMENT | CAT DOMAIN (DELETING THE 19kD INSERT) IN E. COLI; ACTIVE AFTER REFOLDING |
|  | GELATINASE B | 9 | SEE MMP-2 | EXTRACELLULAR | SEE MMP-2, BUT DIFFERENT ON LAMININ-5 AND SUBSTRATE PEPTIDES | SYNTHETIC SUBSTRATE PEPTIDES DESCRIBED IN JBC (269:20952). COMPARISON w/ MMP-2 SEE BBA 1293:259 |  |
| STROMELYSINS | STROMELYSIN 1 | 3 | 166 | EXTRACELLULAR | BROAD: FIBRINECTIN, LAMININ, COLLAGEN II, IV, V, IX, X; PROTEOGLYCAN, ETC. | SYNTHETIC SUBSTRATE PEPTIDES DESCRIBED IN JBC (269:20952) |  |
|  | STROMELYSIN 2 | 10 | 166 | EXTRACELLULAR | SEE MMP-3 |  |  |
|  | STROMELYSIN 3 | 11 | 166 | EXTRACELLULAR, SECRETED AS ACTIVE FORM | SEE MMP-3 |  |  |
| MEMBRANE TYPE MMPs | MT1-MMP | 14 | 173 | MEMBRANE BOUND | ACTIVATE MMP-2? COLLAGENS, ETC. | CLEAVE PROMMP2: 68-64-62 kD. CLEAVAGE SITES ON MMP2, 13 (JBC271:17119, 17124) | PROMMP-14 EXPRESSED IN E. COLI. CAN BE ACTIVATED BY FURIN @ R111 |
|  | MT2-MMP | 15 | 169 | MEMBRANE BOUND | ACTIVATE MMP-2? COLLAGENS, ETC. |  |  |
|  | MT3-MMP | 16 | ? | MEMBRANE BOUND | ? |  |  |

FIG. 8D

| SUBCLASS | COMMON NAME | MMP-# | CAT DOMAIN (a.a., APPROX.) | CELLULAR LOCALIZATION | SUBSTRATE PROTEINS | INFO ON CLEAVAGE SITE SEQUENCES | EXPRESSION IN YEAST OR E. COLI. |
|---|---|---|---|---|---|---|---|
| | MT4-MMP | 17 | ? | MEMBRANE BOUND | ? MAY BE INVOLVED IN ACTIVATION OF GFs, TNFs | | |
| ELASTASE | MACROPHAGE METALLOELASTASe (MME) | 12 | 164 | EXTRACELLULAR, EXPRESSED BY MACROPHAGE | ELASTIN, COLLAGEN IV, IMMUNOGLOBULIN, PHASMINOGEN, ETC. | CLEAVE PLASMINOGEN TO FORM 38kD ANGIOSTATIN | |
| MATRILYSIN | MATRILYSIN | 7 | 165 | EXTRACELLULAR | SIMILAR TO STROMELYSINS? | | PROPROTEIN EXPRESSED IN E. COLI. AS FUSION PROTEIN |
| MMP-18 | | 18 | ? THE A.A. HAS CLOSEST IDENTITY WITH MMP-1, 3, 10, 11 | EXTRACELLULAR | ? | | |
| MMP-19 | | 19 | ? THE TOTAL A.A. SHOW ONLY 28-35% IDENTITY w/ OTHER MMPs | POSSIBLY EXTRACELLULAR. THE TISSUE DISTIBUTION IS SIMILAR TO THAT OF MMP-14 | CLEAVE SYNTHETIC PEPTIDE OF STROMELYSIN SUBSTRATE BUT NOT COLLAGENASE SUBSTRATE | CLEAVE STROMELYSIN SUBSTRATE (PEPTIDE "McaPLANvaDpaARNH2") | PROPROTEIN CLONED IN E. COLI IS INACTIVE; CAN BE ACTIVATED BY TRYPSIN |

FIG. 8E

| PROTEIN FAMILY | SUBCLASSIFICATION | MEMBER | ACTIVE SITE/MUTATIONS | ASSOCIATED WITH DISEASE | DISEASE PREVALENCE | SUBSTRATE(s) | SUBUNIT COMPOSITION | (SUB)CELLULAR LOCALIZATION | SPECIFIC/BROAD SPECTRUM INHIBITOR(s) | PHENOTYPES IN YEAST OR E. COLI? | PHENOTYPE DESCRIPTION | COMPETITION |
|---|---|---|---|---|---|---|---|---|---|---|---|---|
| ION CHANNELS | A. VOLTAGE-GATED | | | | | | | CELL MEMB. | | | | |
| | | 1 NA+ | X | SCN5A, ARRHYTHMIA | RARE | Na | | HEART | | | | |
| | | | X | SCN4, PARALYSIS | RARE | Na | | NMJ | | | | |
| | | | | ANAESTHESIA | NA | Na | | NMJ | LIDOCAINE | | | |
| | | | X | LIDDLE'S SYND.(HD) | V. RARE | Na | | SM MUSC. | AMILORIDE | | | |
| | | 2 K+ | X | HERG. ARRHYTHMIA | RARE | K | | HEART | | | | |
| | | 3 Ca2+ | | AGING | COMMON | Ca | | NEURON | SEVERAL | | | |
| | | | | ALZHEIMERS | COMMON | Ca | | NEURON | | | | X |
| | | | | APOPTOSIS | ? | Ca | | NEURON | | | | |
| | | | | CARDIAC/VASCULAR DIS | COMMON | Ca | | HEART | SEVERAL | | | X |
| | | | | N-TYPE: PAIN, NEUROPROT | COMMON | Ca | | CNS | | | | |
| | | | | IMMUNOSUPRESSION | | Ca | | T CELL | | | | |
| | | 4 Ch | X | CLCN1, PARALYSIS | RARE | Cl | | MUSCLE | | | | |
| | | | X | CFTR, CF | RARE | Cl | | LUNGS, PANCREAS | | | | |
| | B. LIGAND-GATED | | | | | | | NEURON | | | | |
| | | 1 GLU | | NMDA, STROKE | COMMON | | | | | | | |
| | | | | ANALGESIC, NEUROPROT. | COMMON | | | | | | | |
| | | 2 ACh | | ALZHEIMER'S | | | | | | | | |
| | | 3 5HT | | ANXIETY | | | | | | | | |
| | | 4 GABA | | | | | | | | | | |
| | | 5 GLY | | | | | | | | | | |
| | C. ATP-SENSITIVE | | | | | | | VARIOUS | | | | |
| | | 1 P2X | | ATP-GATED, PAIN? | | | | IMMUNE | | | | |
| | | 2 SUR | | DIABETES, INS. SECRETION | | | | BETA CELLS | | | | |
| | | 3 SUR2 | | ? | | | | SM MUSC. ETC | | | | |
| | D. OTHER | | | | | | | | | | | |
| | | AQUAPORINS | | WATER REGULATION? | | | | | | | | |

FIG. 9

SURROGATE GENETICS TARGET CHARACTERIZATION METHOD

This application claims benefit of U.S. Provisional Application No. 60/064,897, filed Nov. 7, 1997.

BACKGROUND OF THE INVENTION

This invention relates generally to the fields of molecular biology and drug discovery. More particularly, the invention relates to identification and evaluation of compounds which modulate the activity of specific biomolecules, including the identification and evaluation of potential therapeutic agents. It also concerns elucidation of gene function(s).

Conventionally, the identification of compounds which usefully modulate the activity of a biomolecule has been performed by either of two methods.

First, biomolecules implicated as playing a critical role in a particular disease are often used as targets in biochemical assays to find specific inhibitors or other modulators of the specific biomolecules. This approach, however, generally requires a great deal of prior research to identify, characterize, and validate the target, information which is unavailable for the vast majority of human genes (or the genes of other commercially important eukaryotic organisms) despite the identification of large numbers of putative coding regions from genome sequencing efforts. As a result, a biochemical assay approach remains unavailable for the majority of potential targets.

Second, screening is often performed using whole cell assays, typically by screening compounds against a cell of interest and looking for compounds which produce a particular readout. This process is often conducted with little or no information on the specific target affected by a particular compound.

Due to the limitations inherent in these conventional approaches, there remains a need for improved techniques for identifying the function of potential target genes and gene products. Additionally, useful targets have been identified, there also remains a need for improved screening techniques to identify potential modulators of these target genes and gene products.

SUMMARY OF THE INVENTION

The present invention provides a method which combines inhibitor screening and target validation in a single process, and thereby provides a more efficient process for identifying new therapeutic compounds and gene functions.

As indicated above, conventionally the identification of compounds which usefully modulate the activity of a biomolecule has been performed using either biochemical assays with validated target molecules, or non-specific, cell-based screening to detect desired cellular responses or readouts.

In contrast, the methods of the present invention provide both a cell-based screening method utilizing convenient surrogate assays and partial target characterization, which can include indication of therapeutic relevancy, thus allowing the identification and use of previously unidentified cellular targets to screen for potential lead compounds. Advantageously, these methods can be applied to the screening and characterizing of large numbers of partially and/or completely uncharacterized genes, thereby providing both combined modulator screening and target screening methods. This combination results in the use of cellular targets which would have been ignored in conventional screening methods due to the lack of specific functional and/or structural information and the large amount of work required to obtain that information.

Thus, the invention provides a method for both determining the cellular function of a gene of unknown function and identifying modulators of that gene, preferably modulators with therapeutic potential. The method involves contacting a first cell population with a test substance, where the cell expresses a biomolecule encoded by a heterologous gene, and determining whether the test substance alters a phenotype of the cell population which is created by the presence of the heterologous biomolecule. Such alteration of the phenotype indicates that the test substance is an actual modulator. A modulator identified in this way can then optimally be used to contact one or more second cell populations which provide a model system for the function of the protein in its natural cellular environment. Such a model system can, for example, be a cell line or cells of an organism naturally expressing the specific biomolecule or a cell line, transgenic animal, or microbial strain which naturally expresses a close homolog of the specific biomolecule and which expresses a recombinant or heterologous copy of the specific biomolecule. Thus, as understood by those skilled in the art, both in vivo and in vitro model systems may be used. The cellular effects resulting from the presence of the modulator are indicative of the cellular function of the protein. Preferably the second cell population provides a disease model and the cellular effects include the effect of the modulator on the status of the disease model or the progress of the disease.

Defined Terms

Unless otherwise expressly defined, the terms used below and in the claims will be understood according to their ordinary meaning in the art, although the following terms will be understood to have the following meanings, unless otherwise indicated.

The term "biomolecule" refers to molecules produced by an organism. Examples of biomolecules include nucleic acids such as DNA and RNA, proteins, carbohydrates, lipids, terpenes, and small molecules such as nucleotides, carbohydrates, and amino acids.

In the context of this invention, "gene" refers to an inheritable unit of genetic material. Each gene is composed of a linear chain of deoxyribonucleotides which can be referred to by the sequence of nucleotides forming the chain. Thus, "sequence" is used to indicate both the ordered listing of the nucleotides which form the chain, and the chain, itself, which has that sequence of nucleotides. "Sequence" is used in the same way when referring to RNA chains, which are linear chains made of ribonucleotides, or to the amino acid sequence of a polypeptide.

In the context of this invention, the term "gene product" or "product of a gene" refers to a biomolecule encoded by a DNA sequence, and is thus an RNA molecule or a protein, but which may undergo post-transcriptional or post-translational processing. Which genes are expressed in a specific cell line or tissue will depend on factors such as tissue or cell type, stage of development of the cell, tissue, or individual, and whether the cells are normal or transformed into, for example, cancerous cells.

A DNA sequence encoding a biomolecule whose function is unknown is referred to as a "gene of unknown function." In this context, "unknown function" may be understood to describe a gene or biomolecule with no apparent homology to any gene or biomolecule with a previously identified function. Alternatively, "unknown function" may describe a gene or biomolecule with a function predicted from sequence homology to a known gene or biomolecule, but where that function has not been confirmed by other means. Typically, homology (or lack thereof) will be determined by comparison to nucleotide or protein sequences in any of the several sequence databanks used by those skilled in the art.

Additionally, "unknown function" may also describe a gene or biomolecule with a previously known function, but which also has at least one function which has yet to be identified.

The DNA sequence encoding the biomolecule may be a complete gene containing all of the necessary information to produce an RNA or protein molecule, or may be a DNA copy of a messenger RNA molecule, known in the art as a "cDNA". Alternatively, the DNA sequence may only potentially encode a portion of an RNA or protein molecule.

"Protein" refers to a polypeptide translated from an RNA, or to a complex which includes at least one such polypeptide in an active complex. Examples include homodimers, heterodimers, multi-subunit complexes, and complexes including prosthetic groups, one or more polypeptides and one or more RNA chains.

In the context of the present invention, a "heterologous DNA sequence" refers to a DNA sequence present in a cell which is derived from another source, including, without limitation, another cell or a virus. Typically in this invention, the heterologous DNA sequence will be introduced into a cell by recombinant DNA techniques or by mating.

Similarly, a "heterologous biomolecule" refers to a biomolecule expressed in a cell which does not normally express that biomolecule, or which is expressed in a cell in a non-natural manner. Typically in this invention, the heterologous biomolecule will be expressed from a heterologous DNA sequence. The heterologous biomolecule may be encoded by a DNA sequence prepared synthetically, or obtained from an organism such as an animal, plant, or microbe. In particularly preferred embodiments, the heterologous biomolecule is encoded by a human DNA sequence or a DNA sequence from a human pathogen, for example, a virus, bacterium, or fungus.

The term "cellular function" refers to a cellular biological effect of a particular biomolecule. This can include the effects of a gene naturally expressed by a cell, e.g., a human cell, but can also include the effects of a gene naturally expressed by a pathogenic virus or microbe. Cellular function includes a biological effect related to the development and/or progress of a disease, e.g., a human disease. Cellular function is distinguished from "biochemical activity", which refers to the molecular interactions in which a biomolecule is involved which relate to the cellular activity of that biomolecule. Thus, the biochemical function or functions of a biomolecule can be exerted in a cell-free system as well as in a cell, while the cellular function or functions can only be present in a cellular environment, which may, in different cases, be in a complex organism, in a tissue culture, or in isolated cells. A cellular function typically comprises several biochemical interactions, for example in a cascade or signal transduction pathway.

The term "disease model" refers to a cellular system which produces observable characteristics correlated with the pathological process of a disease, where at least some characteristics of the system reflect the status of the disease model. Such a model can, for example, include an in vivo system in which a particular disease is developing, or a system which has sufficient similarity to a disease system so that changes in the model system are reasonably correlated with and predictive of effects in a corresponding disease system. The "status" of a disease model system refers to the status of a characteristic of the model system which is indicative of disease behavior, and thus can, for example, refer to the development or pathology of the disease or a condition related to the disease, and to the amount of a particular molecule or molecules in the system, as well as other indicators.

A "human pathogen" refers to a microbe, including both cellular microbes and viruses, which can infect a human organism and produce damaging effects. Such pathogens include both those which can infect normal hosts as well as those which are only capable of opportunistic infection, for example, of injured or weakened individuals.

In connection with identifying modulators of a gene product, the "activity" of the gene product refers to the biochemical activity of the gene product. Modulating the biochemical activity or the biomolecule in vivo will frequently then result in a detectable cellular alteration.

A "modulator" is a compound which alters or modulates the biochemical activity of a particular biomolecule.

A "test substance" is a compound which is a potential modulator. A test substance may be a small molecule, or it may be a macromolecule such as a peptide, a nucleic acid, an antibody, a receptor molecule, or a protein.

A "small molecule" refers to a compound which has a molecular weight of less than about 10,000 Daltons, more typically less than about 5000 Daltons, preferably less than about 3000 Daltons, more preferably less than about 2000 Daltons, and still more preferably less than about 1000 Daltons, and most preferably less than about 700 Daltons. A "potential small molecule modulator" thus refers to a small molecule, as described, which is used as a test substance to determine whether it has modulator activity in a particular test system.

The term "cell population" refers to one or more cells produced from a single parent cell. Such a population of cells is known to those skilled in the art as a "clone". In the context of the present invention, all of the cells in a cell population can be considered identical and therefore express identical biomolecules.

In the context of this invention, a "measurable phenotype" is an observable property of a cell resulting at least in part from the expression of a heterologous biomolecule in that cell, where the level or nature of the observable property changes in response to changes in the activity or expression level of the heterologous biomolecule.

The term "cell growth" refers to the growth or proliferation of a cell population. The term "cell death" refers to the unscheduled or premature death of a cell population. The term "cell differentiation" refers to the process by which cells mature and become less pluripotent, as that term is used in the art. The term also refers to a change of appearance or phenotype as compared to the average subject. The term "cell survival" refers to the unscheduled survival of a cell. Unscheduled or prolonged survival is determined by comparison to otherwise normal, untreated, similarly situated cells.

Cell growth, death, differentiation, and survival are phenomena simply measured by methods well-known in the art. For example, these methods can involve observing the number of cells or the appearance of cells under a microscope with respect to time (for example, days). Typically, these methods involve comparison to otherwise normal, untreated, similarly situated cells.

In connection with contacting a second cell with a modulator, a cell "naturally expressing said protein" or which "expresses the biomolecule as a normal constituent" refers to a cell which expresses the protein or biomolecule without human intervention, which can include the expression of viral biomolecules in an infected cell.

As understood by those skilled in the art, a "biochemical activity class" refers to a grouping of biomolecules in terms of the type of biochemical reaction or process in which the biomolecules are involved. Such classes can include, for example, proteases, signal transduction proteins, ion channels, kinases, DNA binding proteins, and the like. As has been described in the literature, the activity class of many molecules can be predicted or suggested by sequence comparison with molecules having known biochemical activity.

Preferably, the biochemical activity class of the product of the heterologous gene in the first cell is predicted prior to the step of contacting the first cell with a test substance. This is advantageous in guiding the selection of an appropriate expression and measurable phenotype for screening with the first cell. In preferred embodiments, the heterologous biomolecule is a protein with predicted homology to known ion channels, efflux pumps, membrane bound signal transduction proteins, DNA binding proteins, or enzymes, for example proteases, protein kinases, protein phosphatases, and the like. However, the heterologous biomolecule is not limited to these classes of proteins.

Likewise, in preferred embodiments the first cell population is at least one prokaryotic or eukaryotic cell, preferably a bacterial cell or more preferably a yeast cell. However, a cell line derived from a higher organism can be used which does not normally express the specific biomolecule, or which is modified so the normally expressed biomolecule is not expressed, thereby providing a measurable phenotype different from that provided by normal expression.

Introduction of genetic material into the first cell population can be performed using a variety of methods known in the art (e.g., transformation, transfection, conjugation, protoplast fusion, electroporation, particle gun technology, calcium phosphate-precipitation, direct microinjection, mating, and conjugation). The selection of control sequences, expression vectors, transformation methods, and the like, are dependent on the type of host cell used to express the gene.

As used herein, "transformation" relates to transient or permanent changes in the characteristics (expressed phenotype) of a cell induced by the uptake of a vector by that cell. Genetic material is introduced into a cell in a form where it expresses a specific gene product or alters the expression or effect of endogenous gene products.

Transformation of the cell may be associated with expression of a variety of gene products including protein and RNA. These products may function as intracellular or extracellular structural elements, ligands, hormones, neurotransmitters, growth regulating factors, enzymes, chemotaxins, serum proteins, receptors, carriers for small molecular weight compounds, drugs, immunomodulators, oncogenes, cytokines, tumor suppressors, toxins, tumor antigens, antigens, antisense inhibitors, triple strand forming inhibitors, ribozymes, or as a ligand recognizing specific structural determinants on cellular structures for the purpose of modifying their activity. This list is only an example and is not meant to be limiting.

In preferred embodiments, the second cell population comprises at least one prokaryotic or eukaryotic cell, preferably an animal or plant cell, more preferably a mammalian cell, and most preferably a human cell. The second cell population may advantageously be at least one tumor cell, thereby providing convenient growth capabilities. Alternatively, the second cell population may be a permanent cell line derived from an animal, plant, mammalian, or more preferably a human source.

The phenotype created by the presence of the heterologous biomolecule is preferably a growth phenotype, so that a modulator inhibits or enhances the growth of the cell population under at least some culture conditions.

As the method is a screening method, the first cell population can be contacted with a large number of different test substances. In most cases the cell population is contacted separately with individual molecules, for example in separate test compartments. However, assays can be formatted to allow compound pooling, e.g., 2, 3, 4, 5, 10, 100, or more compounds under appropriate conditions.

As the method is applicable to a variety of different heterologous biomolecules, in some embodiments of the invention the heterologous biomolecule is homologous to a biomolecule normally expressed in the first cell population, or is able to functionally complement a biomolecule normally expressed in the first cell population. In other embodiments the heterologous biomolecule has no homolog or functional counterpart naturally expressed in the first cell population. In preferred embodiments, the heterologous biomolecule is at least a portion of an ion channel, an efflux pump or other transmembrane transport protein or complex, a membrane bound signal transduction protein, a protease such as a retroviral protease or other viral protease or a matrix metalloproteinase, a DNA binding protein, a protein kinase, or a protein phosphatase.

Moreover, as the method is applicable essentially all heterologous biomolecules, in preferred embodiments the method involves contacting a plurality of different first cell populations, e.g., 2, 5, 10, 50, 100, 200, or more, expressing different heterologous biomolecules simultaneously with a test substance. Preferably, the plurality of different first cell populations is contacted with the test substance in a single solution. While a variety of different detection and cell discrimination methods can be used to distinguish the different first cell populations in a single solution embodiment, preferably the cell populations have different detectable markers, for example, different length DNA markers or auxotrophic markers, as described in Natsoulis et al., SCREENING METHODS USING MICROBIAL STRAIN POOLS, U.S. patent Ser. No. 08/876,691, and Benton et al., SIZE-BASED MARKER IDENTIFICATION TECHNOLOGY, U.S. patent Ser. No. 08/770,246, both incorporated herein by reference in full, or nucleic acid sequence markers, or combinations of different types of markers.

BRIEF DESCRIPTION OF THE DRAWINGS

FIG. 8A is a table listing representative proteases which can be adapted to use in surrogate phenotype assays, with FIGS. 8B–E providing additional information on certain sub-groups and certain members of those sub-groups.

FIG. 9 is a table listing representative ion channels, along with certain sub-groups and certain members of those sub-groups.

Figure 1A:
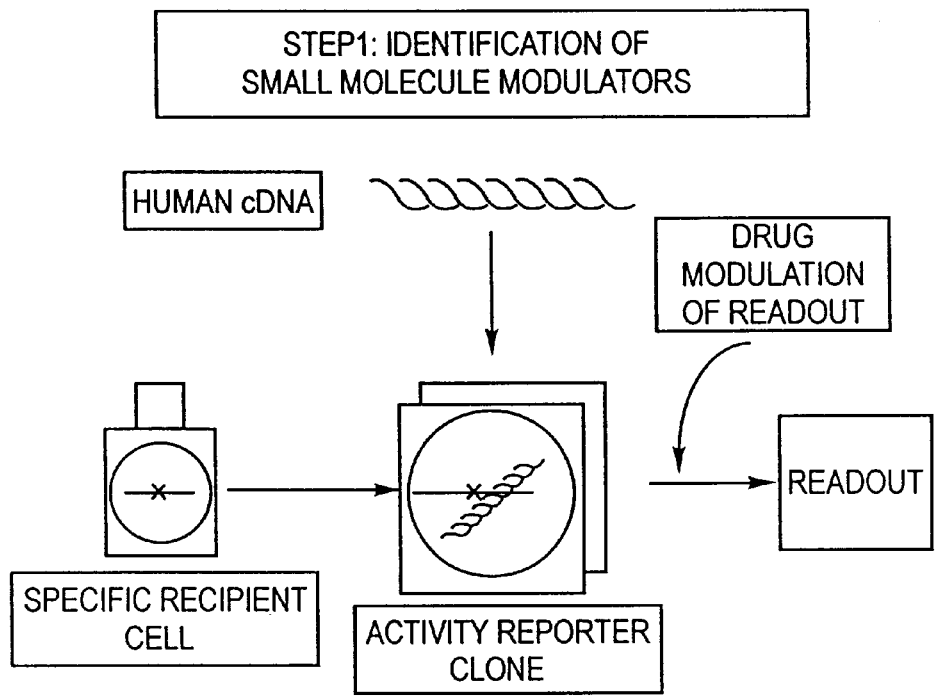
FIGS. 1A and 1B schematically illustrates the two-step method of the present invention leading to the identification of drug leads and gene function.

Other embodiments of the invention will be apparent from the following Detailed Description and from the claims

DETAILED DESCRIPTION OF THE INVENTION

Screening for therapeutically useful compounds has commonly used whole cell screening, in which cells are contacted with a compound under conditions which are believed to be relevant to the intended use of the compound and the cells are monitored for a particular readout which is indicative of an active compound. Such whole cell assays can be carried out utilizing different types of cells. For example, in connection with human genes, natural human cells can be used. Commonly such natural cells are selected to reflect the expected in vivo target cells, but do not provide readouts which are indicative of the particular target biomolecules. Other types of human cells can also be used. Such other types of cells can, for example, have a recombinant gene, be a tumor cell, or otherwise provide an assay cell which differs from the expected target cell but which has useful readout characteristics. Non-human cells, for example, microbial cells such as yeast cells, can also be used for screening assays. Such cells express either homologous or heterologous human genes, and thus provide a "surrogate assay" in which the non-human cell acts as a replacement for human cells and allows compounds to be screened for activity on the human gene or gene product. Often cells are selected which provide more convenient growth characteristics, or more convenient genetic manipulation, or other advantageous experimental characteristics. A number of such surrogate assays have been described, primarily using expression of human genes in yeast cells. While the majority of such assays have involved the expression of homologous genes, a number have been based on the expression of heterologous genes.

The present invention represents a significant departure from conventional assays. Specifically, the invention concerns methods for combining the processes of compound screening and target validation in a single process to identify modulators of genes of unknown function. This process is referred to as "surrogate genetics".

The fundamental concept underlying the surrogate genetics target identification approach is the use of genetics to design assays for various types of human, animal, plant, viral, bacterial, and fungal biomolecules. This approach involves the creation of a variety of heterologous recipient cells that act as reporters of the activity of these biomolecules. The assays themselves serve as sensors to detect modulators that act directly or indirectly on the human, animal, plant, viral, bacterial, or fungal biomolecule. Both the assays and the target-hit correlations (compound "phenoprints") provide important insights into the relationships among genes, including how they work together within a metabolic pathway and allows the best targets from a drug intervention standpoint to emerge from the screen.

As an example, it has been roughly estimated that in humans approximately 5,000 genes out of a total of approximately 100,000 genes could potentially serve as therapeutic targets. Of these, only a few hundred are currently being examined as potential therapeutic targets. It is believed that many of the potential targets have not yet been identified. The present method thus enhances the efficiency and range of usage of potential targets by providing new surrogate assays and a two step process in which a chain is used to provide a surrogate assay for compound screening and one or more active compounds from the screening are used in an in vivo or in vitro model system to characterize the function of the gene.

While the discussion herein is principally directed to the use of human genes, those skilled in the at will recognize that the methods are applicable to genes from other sources, including, for example, other mammals, animals, plants, viruses, bacteria, or fungi.

Until recently, the bulk of the genomics effort has centered on discovering, characterizing, and validating targets. This last step, target validation, is particularly critical because most current approaches are only tending towards function. Sequence homology may, at times, give probabilistic clues as to function, differential display yields correlations among genes, and existing in vitro and in vivo models are cumbersome and inexact. If one can first determine the true function of genes, then the next task is to construct an assay to find specific inhibitors of these pharmaceutically relevant targets.

Thus, what is generally an extensive effort, i.e., to develop a valid assay and find a specific inhibitor in that assay, is justified by the function of that target. This difficult path, from target justification to drug discovery, severely limits the number of assays and potential drug leads that are developed.

Once a modulator of gene function has been identified by the described methods (i.e., a "lead" compound), it may be subjected to further refinement or optimization. For example, with respect to lead compounds which possess potential pharmaceutical activity, that compound is typically selected for a program of medicinal chemistry to generate the compound(s) actually tested as a drug. The drug will preferably be formulated and optimized for use in treatment of disease in the animal, plant, or human. Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or drug cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Drug cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD, D5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Figure 1B:
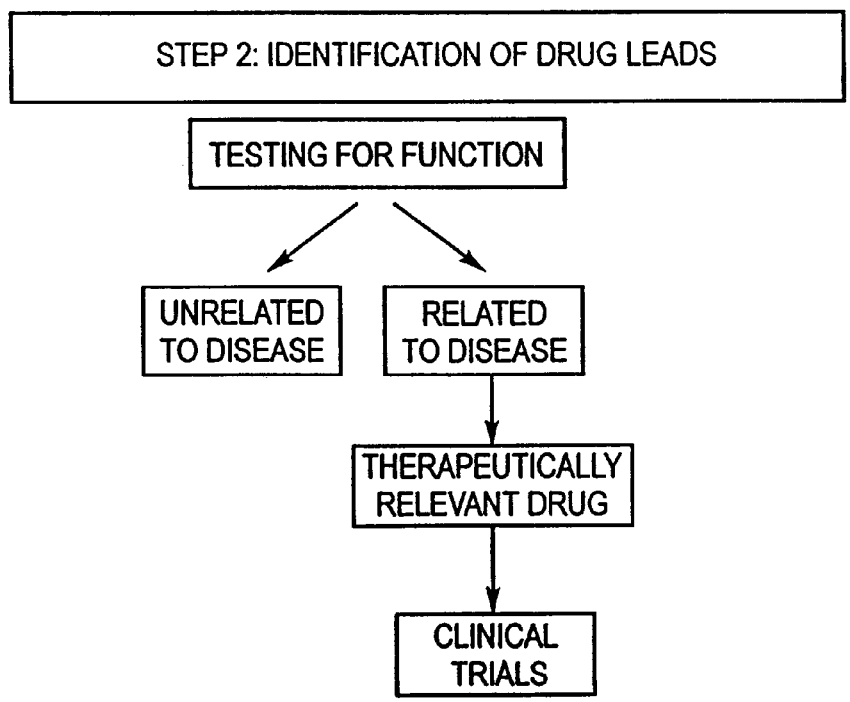

The methods of the present invention bypass the conventional approach to the process outlined above. Instead, the instant methods are amenable to rapid parallel approaches aimed at the simultaneous identification and screening against a greater number of targets. This approach comprises two steps: Step 1 identifies modulators of gene activity, and Step 2 provides a method to determine which of the identified modulators are drug (or other active compound)leads. These two steps are shown schematically in FIGS. 1A and 1B.

In the first step, assays are created by designing the appropriate recipient microorganism such that expression of a specific gene of interest causes a phenotype. These clones (recipient cell expressing a heterologous DNA sequence) are referred to as Activity Reporter Clones (ARCs) because they provide a readout of the activity of the DNA sequence being expressed. In preferred embodiments, ARCs can monitor cell growth, although the range of phenotypes useful in the practice of this invention is not limited to this parameter, as any phenotype that produces a detectable readout can be employed. The ARCs provide the assay for compound screening by allowing monitoring of changes in the readout (in a preferred case, cellular growth) of the ARCs as the result of interaction with a modulating compound. This Surrogate. Genetics approach, does not require complete characterization of genes in terms of function and involvement in disease. Furthermore, the assays are inexpensive, rapidly implemented, and of high-fidelity. Importantly, the nature of the assays allows screening for modulators against a plurality of potential targets simultaneously in a cost effective manner. Thus, the product of Step 1 of the instant methods is the identification of a modulator or modulators of the activity of the biomolecule encoded by the gene of interest.

The second step allows one to distinguish which of the various modulators isolated represent lead compounds. In the instance of lead compounds for human, animal, or plant therapeutics, this is accomplished by testing the effect of the modulators in pharmacological models of various diseases. Some modulators identified in the first step may have no detectable effect. Others affect disease progression, such as by enhancing or by reversing the disease's progression. Both outcomes are useful tools to investigate the function and relationship to disease. Modulators that reduce disease progression constitute leads for drug development.

The two-step Surrogate Genetics process effectively bypasses several early bottlenecks of conventional drug development. The first step identifies putative specific modulators of many gene targets without requiring extensive knowledge of the function of these targets. The second step determines which molecules have a desired therapeutic effect.

Step 1: Isolation of Modulators of Gene Activity
A. Assay Generation

One element to successful implementation of this Surrogate Genetics invention concerns creation of drug screening assays for a large number of genes by designing Activity Reporter Clones (ARCs). ARCs are engineered recipient cells (e.g., prokaryotic or eukaryotic cells) displaying a phenotype caused by the expression of a specific gene, preferably human genes. For example, ARCs have been designed to be reporters of changes in growth patterns, but other cellular patterns such as cell adhesion or differentiation could also be monitored. ARCs are preferably designed either by selection for growth (Rescue), for non-growth (Interference), or for action on an engineered substrate linked to growth (Reporter-Linked). Of course, numerous other ARCs having other phenotypic readouts can be generated using the techniques described herein.

Generally, in a Surrogate Genetics assay according to the invention, the phenotype generated by the presence of a heterologous biomolecule is due to the normal biochemical activity of that biomolecule acting in a foreign cellular context, e.g., on a substrate in the surrogate cell which will, in many cases, differ from the substrate in the biomolecule's native cellular environment. Thus, for example, if the biomolecule is a human protein kinase, it is likely to phosphorylate one or more proteins in a yeast host cell (when a yeast cell is used as an ARC) which are different from the proteins normally phosphorylated by the kinase in the native human cell. The phosphorylation in the yeast cell will generally then create a phenotype which is produced by the normal biochemical activity of the protein kinase but which is generally unrelated to the cellular function of the, protein kinase in its native cellular environment.

This aspect of the assay should be distinguished from a non-specific phenotype generated by the presence of a heterologous biomolecule. Such a phenotype could be generated in a yeast cell by interactions of the heterologous biomolecule unrelated to its usual biochemical activity. As an example, if the heterologous biomolecule accumulated and blocked yeast nuclear pores, and this was unrelated to the normal activity of a biomolecule, reversal of the effects of nuclear pore blockage by a compound would not provide a modulator of a biomolecule because that effect is unrelated to the normal in vivo biochemical activity of the protein.

1. Selection of Genes That Functionally Replace Mutated Genes in the Recipient Cells Herein, genes which rescue recipient cells from death. for example by allowing growth of auxotrophic cells in deficient media, or by permitting growth of other cells in toxic media, are termed "Rescue ARCs". As an example, a yeast strain carrying mutations in two potassium ($K^+$) channel proteins has previously been used to identify cDNAs encoding $K^+$ channels from the plant *Arabidopsis thaliana* and from cardiac tissue, both of which restored $K^+$ uptake. Thus this approach can be used to identify assays for all those genes that functionally compensate for mutations in various cellular pathways in yeast. Some of these genes have been described in the X-ref database and others in the literature, and currently number approximately 100. Thus, the present invention provides assays for all those biomolecules that have either been described as functional homologs or that are predicted to be functional homologs based on sequence homology with yeast biomolecules.

Figure 2:
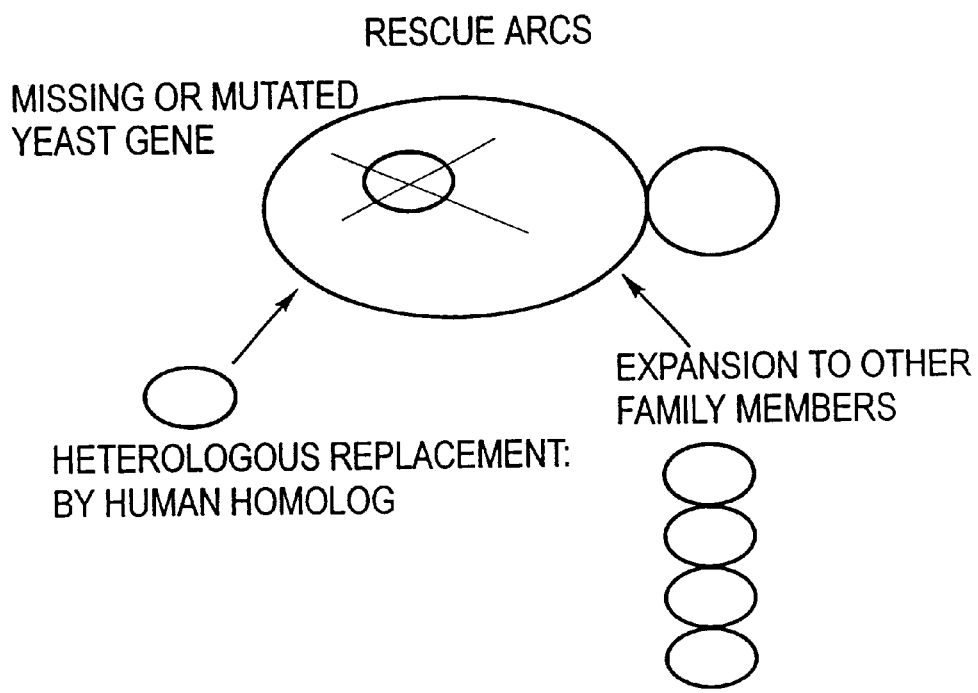
FIG. 2 is a schematic showing the use of rescue ARCs and the expansion from an initial heterologous gene replacement to other members of a gene family to which the initial gene belongs.

Moreover, the present invention permits identification of genes which exhibit no sequence homology to any yeast gene, but which nonetheless functionally compensate for a mutation in a yeast cellular pathway. FIG. 2 schematically depicts a Rescue ARC. On the left is the gene that functionally replaces the mutated or deleted yeast protein. On the right (expansion to other family members) shows that other functionally similar proteins will also rescue cellular growth. Expansion to other family members occurs by choosing individual cDNAs that are functionally similar (using information from existing databases), or by transformation of the Rescue ARC with a random cDNA library.

2. Screening for Genes That Specifically Interfere With Cellular Growth: "Growth-Interference ARCs"

Figure 3:
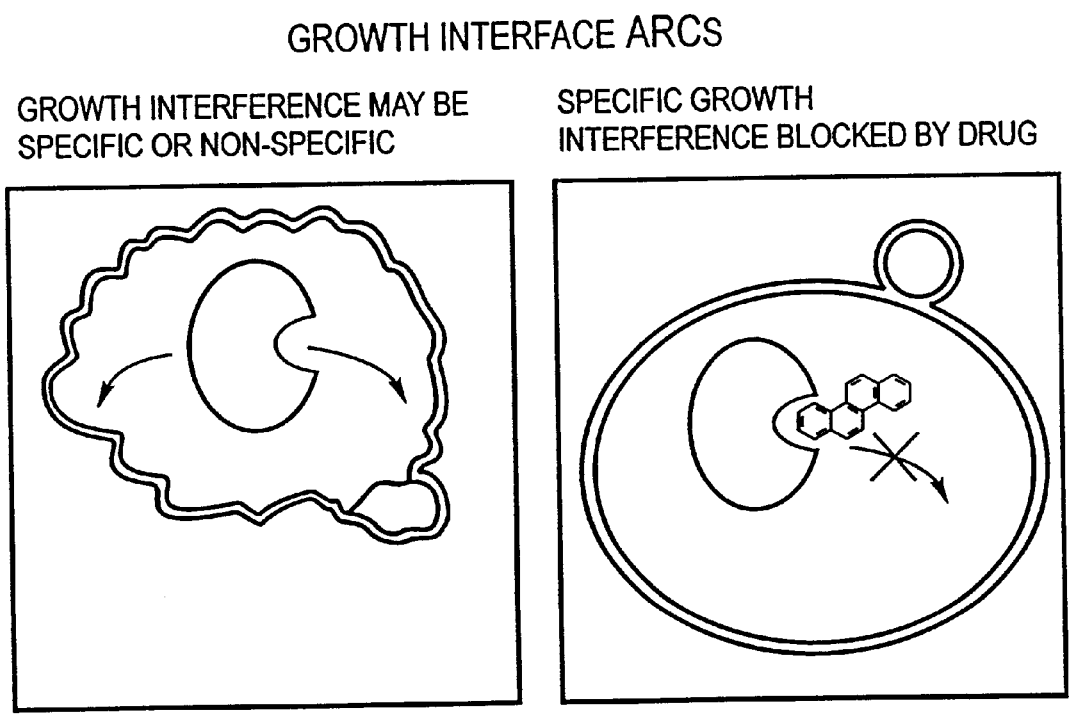
FIG. 3 is a schematic drawing of the action of a growth interference ARC, specifically illustrating specific interference at the active site of a protein.

FIG. 3 depicts a biomolecule specifically interfering with growth through its active site. Possible growth inhibition via non-specific interference not related to the normal activity of the protein could occur, and is also represented. A series of validation techniques is used (described below) to identify interactions occurring via the active site.

An example of assay creation based on a family of functionally related genes is the creation of assays for the $Ca^{2+}$ channel family. For example, expression of the human $Ca^{2+}$ channel in wild-type yeast may be toxic to yeast because $Ca^{2+}$ is normally kept low in the cytoplasm. If no phenotype is observed because the cell tolerates increased $Ca^{2+}$ levels, then the effects of elevated $Ca^{2+}$ levels can be reported by inducing the expression of a $Ca^{2+}$-dependent nuclease in the cytoplasm. A candidate for such a reporter substance is the *Staphylococcus aureus* nuclease which cleaves RNA and DNA. The nuclease can be expressed in the ARC for use as an indirect reporter of human calcium channel activity. Elevated $Ca^{2+}$ levels caused by expression of the human $Ca^{2+}$ channel would induce the activity of the nuclease, which would result in rapid degradation of RNA in the cytoplasm, which would be toxic to the cells. This assay can be expanded to other $Ca^{2+}$ channels by transforming the strain with a cDNA library.

Figure 4A:
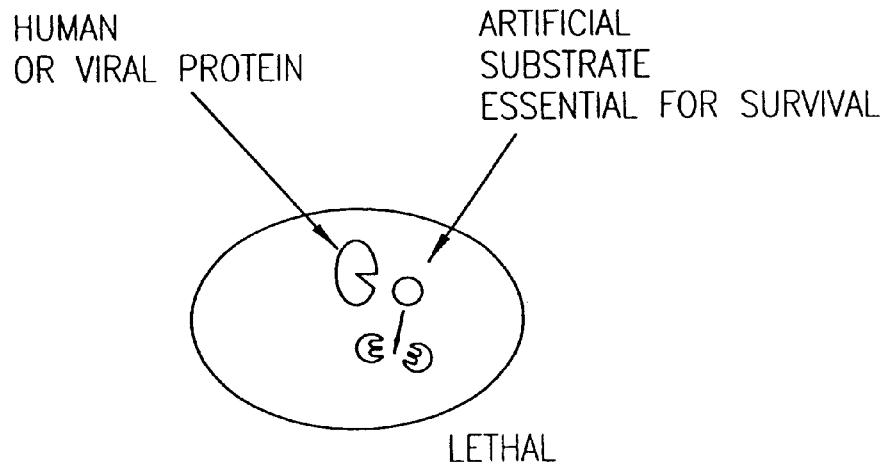
FIG. 4A schematically illustrates a reporter-linked ARC, showing the action of a protein on an artificial substrate in a cell.
Figure 4B:
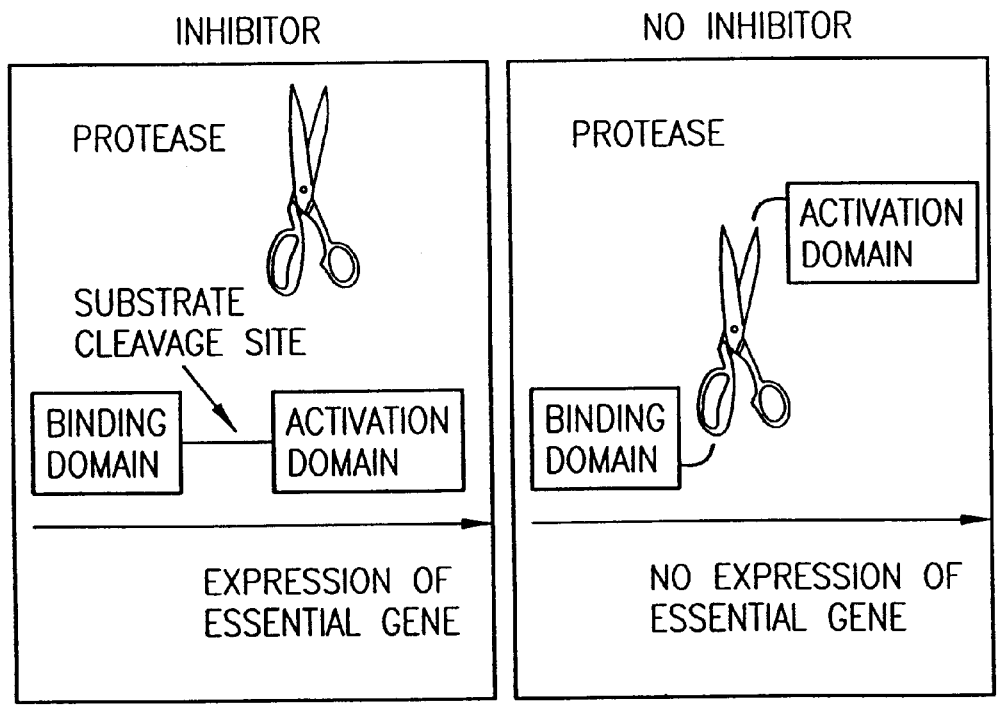
FIG. 4B illustrates the design of a protease assay in an exemplary reporter-linked ARC.

3. Screening or Selecting for Genes That can Act on Artificial Substrates Expressed in the Recipient Cells As an example of this approach to ARC generation, genes encoding proteases for which the substrate cleavage site is known or predicted by sequence homology with a known protease can be used. Particularly preferred are human genes which encode or are predicted to encode proteases. The cleavage of the substrate is a measure of the activity of the protein and is linked to cellular growth. We refer to these assays as "Reporter-linked ARCs". This approach is shown schematically in FIG. 4A, and an example using a protease with known cleavage site is shown in FIG. 4B.

4. Using the Assay Creation Toolbox to Develop Anti-viral Assays

The Surrogate Genetics methodology, which can also utilize genetic potentiation techniques, allows the exploitation of a variety of possible drug targets. The power of this approach is that ARCs, including those described above, can create assays (the basis for compound screening) for a broad set of potential targets that include human, animal, plant, viral, and microbial genes. Viral or microbial assays enable screening for modulators of those targets, leading to the initiation of pharmacological studies on these putative targets. This set of genes includes: 1) initial proven viral targets such as HIV protease, 2) potential targets, such as viral open reading frames, that are not validated either by existing antiviral agents or discovery programs, and 3) novel viral targets for which ARCs are obtained.

Figure 5A:
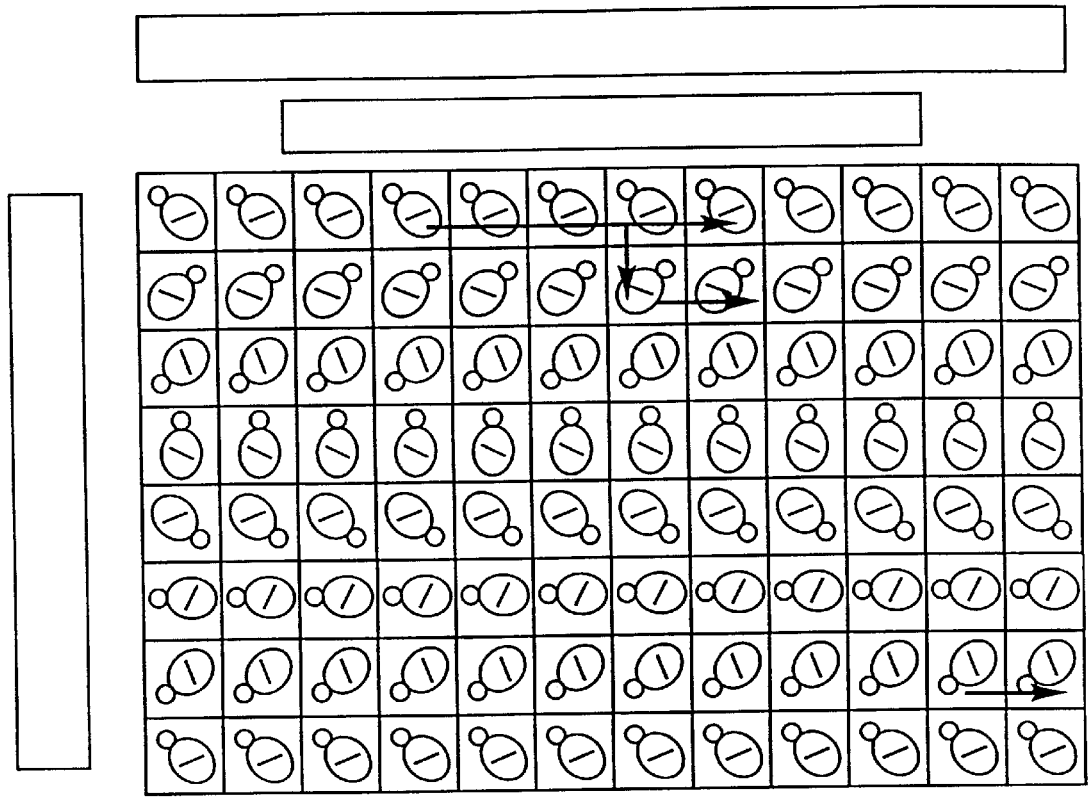
FIG. 5A illustrates the use of an ARC matrix in which a number of different cDNAs are expressed in a set of specific recipient cells to obtain reporter clones for use in the compound screening step.
Figure 5B:
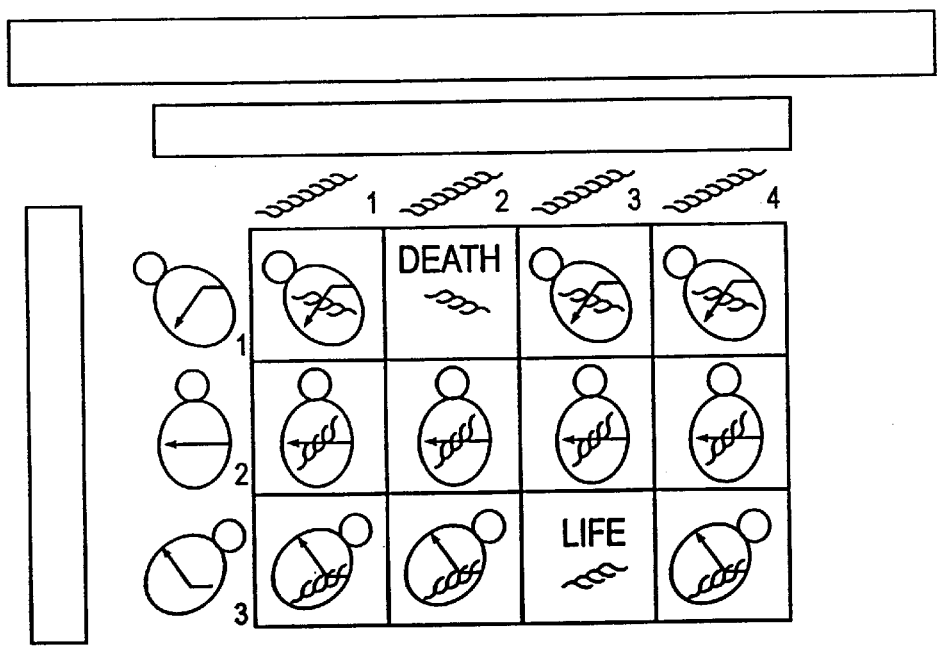
FIG. 5B illustrates the expansion of the matrix by the inclusion of cDNAs from genes for other functional family members.

5. Assay Generation via the Surrogate Genetics Platform Results in a Powerful Information Resource, the 2D ARC Matrix The methods of this invention can be used to create assays for many, or even all, genes from an organism, preferably animal, plant, viral, bacterial, and fungal genes, and more preferably human genes. Creation of such a broad range of assays involves the identification of many different assay conditions for the various genes. To do this, a specific manipulated recipient cell population or ARC is designed, in which a DNA sequence generates a phenotype (see FIG. 5A, DEATH and LIFE). The phenotype is the basis for a compound screening assay. To find conditions that enable a given DNA sequence to be used in an assay on a one-by-one basis is laborious and inefficient. Thus, a strategy has been developed to intelligently design assays. This strategy is achieved through the initial selection of ARCs and heterologous DNA sequences that give a high probability of obtaining a phenotype. Once the appropriate ARC for a given DNA sequence is identified (e.g., $K^+$ channels), the assays are expanded to include other functional family members (see FIG. 5B on expansion and ordering). This expansion can be random (via transforming a cDNA library into a specific ARC) or ordered (by choosing individual cDNAs from existing databases that are predicted or known $K^+$ channels, for example).

The ARC matrix provide tangible assays for compound screening; identifies assays for a large number of genes that may or may not be based on prior understanding of the function of the gene of interest; provides information about genes with known function by elucidating the combination of one of many defined genes with one of many possible recipient cells that produces a phenotype; and defines the functional relationships between recipient cells and the genes being expressed, allowing assays to be designed and performed with other family members of those genes.

B. Assay Validation

In order for the Surrogate Genetics approach to function properly, the activity readout of the ARCs should be specific, such that the phenotype exhibited by the cell population is caused by the activity of the biomolecule of interest. Since the biomolecule is being expressed in a foreign cell, there is a distinction between its activity in the foreign cell and its native function. For example, reproduction of the normal activity of a protein kinase, phosphatase, or protease in a foreign cell does not constitute native function. The enzyme in the native environment is part of a cellular pathway regulated in time and space and acts on a "specific" substrate. For example, validation is needed to ensure that a human protease expressed in a foreign cell causes a phenotype that is directly related to its proteolytic activity. Thus, the phenotype produced in the ARCs is preferably validated as being caused by the activity of the biomolecule expressed from the heterologous DNA sequence, as described below.

Toolbox for validating those phenotypes where the structure or activity of the gene product is known.

Representative examples of validation of the phenotype of an ARC concern mutagenesis. As those in the art will appreciate, many other phenotypes can be validated in accordance herewith.

1. Active Site Mutagenesis

Figure 6:
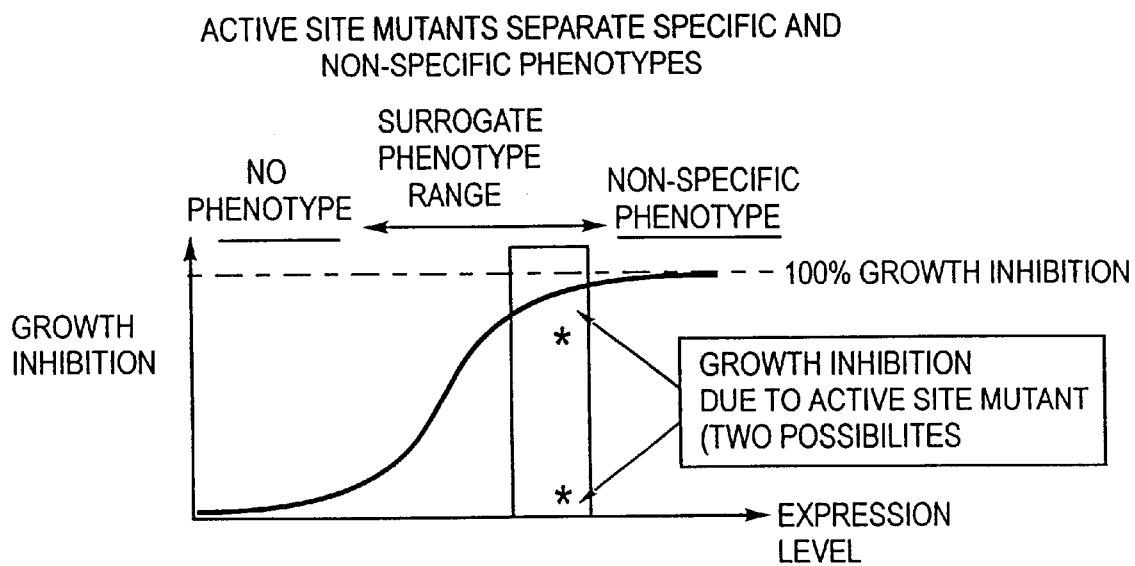
FIG. 6 schematically, in the case of a growth inhibition assay, the range of expression levels and range of growth inhibition which provide useful surrogate phenotype compound screening.

The growth phenotype caused by expression of a heterologous gene (or open reading frame) in an ARC will vary with the cellular concentration of the encoded biomolecule (FIG. 6). For optimum screening, the level of gene expression should be the lowest concentration that causes the maximum growth phenotype. If too much expression occurs it is difficult to modulate by screening compounds, while too little expression does not yield a clear phenotype.

The phenotype attributable to the heterologous DNA sequence may or may not occur through the active site of the biomolecule expressed therefrom. In one embodiment, this can be readily tested if the active site of the expressed biomolecule is known or can be predicted. Active-site mutations can be constructed to test the specificity of the ARC phenotypes. Alternatively, if the active site is not known or predicted, random or site-specific mutagenesis can be performed on the heterologous DNA molecule, or a portion thereof, and mutations can be detected which cause an alteration in the activity of the biomolecule. Regions containing such mutations can be further mutagenized, if necessary. If the phenotype is due to the activity of the biomolecule, the biomolecule carrying the mutation should be unable to cause a growth phenotype (see FIG. 6). Any growth inhibition remaining under these conditions is defined as the non-specific component of the phenotype (FIG. 6).

2. Expression Rheostat

In order to produce the level of gene expression required to meet the goals discussed above, it is preferred to produce a constant level of the biomolecule in the ARC, at least under assay conditions. Importantly, tight regulation of expression is preferred because the phenotype produced may be potentially toxic. Thus, if the baseline expression from the heterologous DNA sequence is not tightly controlled, biomolecules with the greatest toxicity would be selected against. Engineered expression vectors allow ARC phenotypes to be correlated with the expression level of the biomolecule, in a manner that is optimal with respect of the biomolecule specific activity. Such vectors act as rheostats to control the level of expression of the gene encoding the biomolecule, its stability over time, and give a zero-baseline of expression.

3. Data From The Matrix

Information from the ARC matrix helps determine whether the surrogate phenotype is valid. For example, if a cDNA encoding a putative transporter (determined, for example, by sequence homology or predicted protein structure)rescues several transporter-deficient yeast strains, the phenotype is likely to be related to the normal activity of the human protein.

4. Cell Biological Assays

These assays allow the monitoring of changes in ARCs as a result of expression of biomolecules. Examples include intracellular ion concentration, intracellular localization of human proteins, and others.

Toolbox for validating ARC phenotypes where the activity of the gene product is unknown.

5. DNA Arrays

For cases where the active site of the expressed human gene is unknown, DNA array technology can be used as part of the validation toolbox to define the specificity of the phenotype produced. DNA arrays provide efficient screening over a large number of microbial strains or cells lines. The present invention will use DNA arrays in a variety of settings to investigate cellular responses at the genome level.

Whole genome arrays have been described for *S. cerevisiae*. These arrays are composed of elements representing all yeast open reading frames. Using probes derived from RNA extracted under various conditions, one can determine in a single hybridization reaction the transcriptional effect of a particular growth condition on all the genes of the organism.

DNA arrays can be employed to detect the phenotype, in essence taking the RNA transcription level of some or all of the host cell's genes as the "phenotype", and considering each examined RNA molecule as a reporter molecule

C. Compound Screening

1. Strain Multiplexing as a Mechanism to Increase Throughput

An important attribute of Surrogate Genetics is the use of assays for large numbers of genes. If assayed individually, the total number of assays to be performed is the product of the number of assays (>>100) by the size of the compound library (>>100,000). Even with simple whole cell growth assays, the total number of assays required quickly outstrips the capacity of the highest throughput robotic system currently available. In contrast, Surrogate Genetics can utilize a multiplex screening format that essentially collapses the screening matrix down to a single well.

Multiplexing in this context requires that each Activity Reporter Clone be tagged with one or more specific DNA sequences, typically ranging from about 20 to about 100 or more nucleotides flanked on either side by primer binding sites to facilitate rapid amplification of the tag sequences. However, as those in the art will appreciate, any tag can be used which allows one ARC to be distinguished from an ARC harboring a different heterologous DNA sequence. The tag is preferably integrated into the genome of the ARC, although it can also be included on the vector carrying the heterologous DNA sequence, and in some instances it need not be amplified prior to detection. The only requirement for the tag is that it can be specifically detected by molecular hybridization, for example, by a nucleic acid amplification technique followed by hybridization, or by hybridization to nucleotide-sequence-specific array which allows identification of multiple specific nucleotide sequences, and that there is no cross hybridization between tags. A plurality of the tagged strains can be combined to generate one or more master pools. These pools can then be grown under conditions where the biomolecule(s) of interest is (are) expressed.

To enable screening of a master pool containing a plurality of different ARCs against a plurality of test substances, the master pool is then split into as many aliquots as there are compounds to be tested. Each master pool aliquot is then exposed to, contacted with, or grown in the presence of one test substance. At the end of the growth or exposure period, the representation of each tag (i.e., each ARC) can be determined by recovering all the tags and using them as a mixed hybridization probe against a DNA array composed of the tags themselves. In such a format all the targets (i.e., biomolecules encoded by heterologous DNA sequences) can be assayed simultaneously, in the same tube, against one compound. In such a Multiplex Screen, one can detect an increase or decrease in the representation of a tag, i.e., a reversal or an enhancement of growth, at the same time. The sensitivity and the capacity or array technologies to detect nucleotide sequences is several orders of magnitude larger than the anticipated needs of the methods of this invention. However, further expansion of the instant methods to take advantage of such technology is readily within the skill of the art based on the instant teachings.

2. Screening the ARC Matrix With Test Substances

The screening of the ARC matrix with multiple test substances provides a number of potential leads for further evaluation and development, e.g., as therapeutics, insecticides, herbicides, etc., depending on the screen being performed. Additionally, valuable information will be gained during the test substance screening of ARCs about the functional relationships of the genes being expressed. Presumed functional classes of biomolecules obtained by expansion of an ARC, via a cDNA library, are found in the x-direction of the matrix. These are validated if any compound hits most of the ARCs belonging to that functional class, but not those expressed in other ARCs. If a compound hits two different ARCs it identifies a functional relationship. There are two types of functional relationships: those between the cDNAs (x-direction) and those between the recipient cells (y-direction). Those compounds that only recognize a single ARC are highly selective. A unique aspect of compound screening is elucidating the function of a gene (or ARC) where nothing is known about either the biomolecule being expressed or the mutation carried by the recipient cell. If it hits along the x-axis it identifies functional relationships between the biomolecules. If it hits along the y-axis it identifies functional relationships between recipient cells. This aspect of Surrogate Genetics allows the identification and understanding of the function of novel targets that have not been previously obtained by other more conventional approaches.

D. The product of Step 1: Specific Modulators of Activity Reporter Clones

The products of Step 1 are modulators of the activity of one or more biomolecule expressed in one or more different ARCs. The activity of the biomolecule being expressed in the ARCs is not analogous to the native function of the biomolecule since its expression occurs in a heterologous cell. Thus Step 2 of the approach, described below, discerns which of potential modulators identified represent viable drug leads.

E. Step 2: Discerning Which of the Modulators Identified in Step 1 are Viable Drug Leads Step 1 of the instant invention will allow identification of one or more specific modulators from a broad spectrum of biomolecules, rapidly and in parallel. Step 2 directly establishes which of these modulators represents compound (e.g., therapeutic compound) leads meeting the criteria below, by evaluating the effects of these compounds in pharmacological models of disease. Preferred are models of human disease, but the methods of the invention are also applicable to veterinary or plant disease models. Further, in the context of screening for compounds having potential therapeutic utility, Step 2 provides a method to distinguish targets (and their corresponding modulators) with clinical relevance from those which have no obvious role in disease. The result of this process is a set of validated drug leads for pharmaceutical development, including optimization by a program of medicinal chemistry.

F. Properties of Successful Therapeutic Targets

Targets Will Preferably Have the Following Characteristics:

1. Easily Assayed

For a target gene to be productive in a drug discovery program, it must be possible to devise a chemical assay for the activity of the biomolecule(s) encoded thereby. It may be difficult or impossible to develop an assay for biomolecules encoded by certain disease genes, since assays can be created for only a subset of the classes of biomolecules in the genome. Some of these established target classes include the enzymes, receptors and ion channels. Significantly, use of this invention allows empirical identification of novel target classes among all genes that can be assayed.

2. Critical to Disease Pathogenesis

Some disease-linked genes may be important in genetic susceptibility but may have little role in pathogenesis. For example, the subtle variation/mutation at the HLA locus is a major risk factor for autoimmune diseases, including multiple sclerosis and type I diabetes. Nonetheless, at present it is not believed that HLA genes do not represent useful biochemical pathways for therapeutic intervention.

3. Possible to Modulate Activity

In those cases where modifying the activity of a disease gene, or a gene the expression of which may be associated with a disease, may have therapeutic benefit, the relevant encoded biomolecule may nonetheless represent a less-than-ideal target. For example, due to the difficulty of disrupting protein-protein interactions, proteins that engage in novel protein contacts are poor chemical substrates. In such cases, it may be more effective to target biomolecules elsewhere in the particular biochemical pathway.

4. Can be Appropriately Modulated (Activated vs. Inhibited)

In some diseases, inhibition of target activity is desirable for therapeutic benefit; in others, activation of the biomolecule is required. However, it may not be equally straightforward to identify both specific inhibitors and specific activators of a given biomolecule. Instead, it may be technically expedient to increase the activity (activate, agonize) of certain targets and decrease the activity (inhibit, antagonize) of others. Therefore, it is important that the modulator have an effect on the activity of the biomolecule in a therapeutically meaningful way. For example, the neuronal metabolic enzyme acetyl cholinesterase (AChE) is an important inhibitory target in Alzheimer's disease; however, activators of this target are not therapeutically useful, and might be expected to exacerbate existing dementia. Since it is often more straightforward to inhibit a target's activity, the initial focus is on targets whose inhibition is of medical interest.

G. Evaluating Modulators in Pharmacological Models of Disease

Therapeutically-important modulators can be discriminated from other specific inhibitors by their ability to reverse disease processes. Multiple in vitro and in vivo models of disease can be utilized to test the activity of specific modulators of candidate genes for that particular disease. Preferred are models of human disease, but the methods of the invention are also applicable to veterinary or plant disease models.

These pharmacological models of disease processes include whole animal or plant, as well as tissue culture models. Drug leads will be identified from the set of compounds that are shown to alleviate disease processes. Since it confirms a role for a specific target in a specific disease, this method also provides a validation of target function and relevance to the pathophysiology of that disease.

Figure 7:
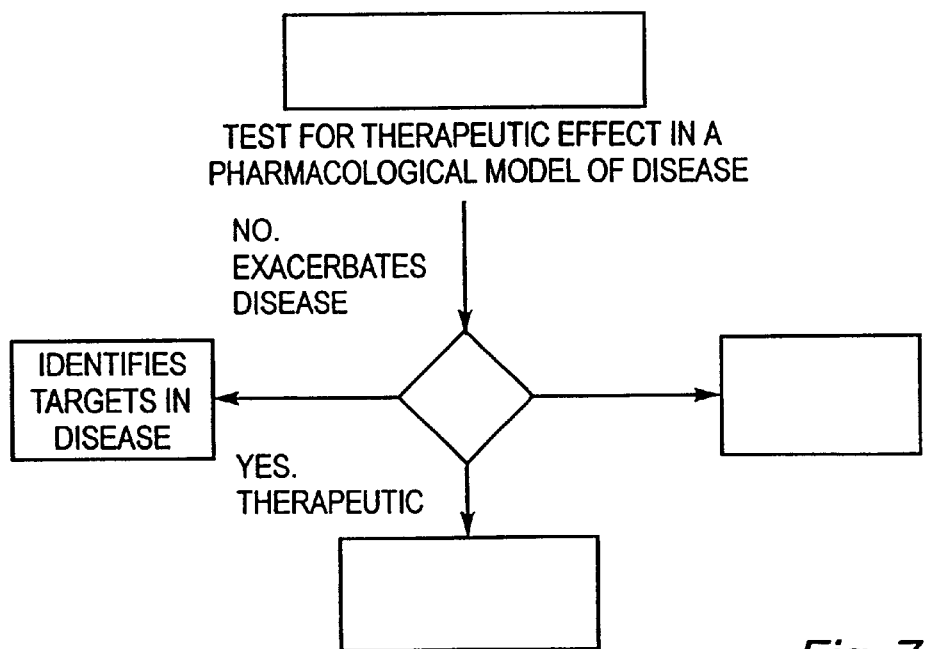
FIG. 7 schematically illustrates a decision tree and the resulting information from the use of specific modulators identified in the compound screening step of this invention when those modulators are used in a disease model system in the second step of the invention.

Compounds that have no obvious effect on the disease process are retained for future data mining and testing in other disease models. Compounds that exacerbate the disease process support the target's involvement in the disease, and suggest that therapeutic benefit may be instead derived by a reversal of the compound's activity. Compounds which successfully modulate pathological processes in these models are tested in additional in vivo or ex vivo models of the disease. These compounds are a valuable source of future drugs leads, and proceed to medicinal chemistry and clinical trials. This decision and information tree is shown in FIG. 7.

H. Pharmacological Models of Human Disease: Three Illustrative Examples

To illustrate the use of specific modulators to establish a target biomolecule's therapeutic relevance, three examples of clinical pharmacological models are given. The examples of clinical pharmacological models have been chosen to represent human diseases, but also preferred are pharmacological models representing diseases of animals and plants for example. These in vitro and in vivo models are presented for reference understanding, and need not represent the actual disease chosen for future pharmacologic development.

1. Diabetes: A Complex Disorder With Multiple Disease Pathologies

The most common type of diabetes, NIDDM (non-insulin dependent diabetes mellitus) affects 16 million adult Americans, and is responsible for 178,000 deaths each year. While diabetes accounts for approximately $91 billion dollars in annual U.S. medical spending, treatment of this disease has not improved dramatically in the past decade.

The large number of metabolic pathways found to be abnormal in diabetic patients illustrates several potentially important sources for therapeutic targets. In addition to characteristically elevated blood sugar levels, diabetic patients frequently have abnormally high hepatic glucose production, impaired glucose tolerance, insulin resistance, obesity, and a spectrum of cardiovascular and neurological differences as compared to non-diabetic individuals. A number of in vitro and in vivo models exist for each of these pathogenic processes, and over fifty candidate genes for NIDDM have been identified for testing in these models. These genes include the glucose transporters, energy expenditure genes, genes involved in lipid metabolism and adiposity, and two genes (hepatic nuclear transcription factors) recently implicated in an early-onset form of diabetes.

To determine which of these targets has a diabetogenic role, specific modulators of these targets can be tested on induced and genetic models of diabetes. Existing mouse and rat diabetes models display varying degrees of insulin secretion, insulin resistance, and obesity. The finding that chemical modulators affect a specific subset of these animal models may help pinpoint the function of the target in pathogenesis. For example, modulators with therapeutic effects on animal models of obesity, without obvious effects on insulin secretion, my help differentiate targets involved in these two diabetogenic mechanisms. Cell culture models include hamster insulinoma cell lines (to examine insulin secretion), and cultured adipocytes (to study glucose transport and vesicular trafficking). Most importantly, compounds that reverse any of these critical pathologies will be extremely valuable future therapeutics.

2. Cancer: Targeting Cellular Growth and Invasion

Like diabetes, cancer is a heterogeneous set of diseases in which multiple cellular processes are perturbed. In most types of cancer, genetic causes are not well established but are considered complex and polygenic. Cancer is thought to result from multiple rounds of mutation in somatic tissue, such that each somatic event increases the ability of the cancer cells to proliferate and metastasize. Three broad classes of cancer genes are recessive tumor suppressors (genes that ordinarily function to slow cell growth), dominant oncogenes (genes which promote proliferative activity), and mutator genes (which result in genome instability and an elevated rate of mutation).

Approximately one in every four deaths in the United States results from cancer; together, all forms of cancer treatment account for over $104 billion in U.S. spending. As a leading cause of death, second only to heart disease,. cancer is very poorly treated. Nonsurgical interventions including chemotherapeutic agents and radiation therapy are often associated with high levels of general toxicity. Current therapeutic targets include the pathways of cell growth and proliferation, apoptosis (programmed cell death), certain human hormones (for hormone responsive cancers), and the immune system. The goal of the NIH funded Cancer Genome Anatomy Project (CGAP) is to identify novel genes and pathways in cancer susceptibility.

Modulators of these and other gene targets identified in accordance with the instant methods can be tested on in vivo and in vitro models of cancer. In vitro models include angiogenesis (tumor supplying blood vessel formation and growth), metastasis (tumor cell invasion of supporting cells), cell cycle progression, and apoptosis. Additional pharmacological models include in vivo genetic and induced animal tumor models, and readouts of characteristic genome expression profiles in tumor tissue (for example, using DNA micro arrays).

3. Viral Diseases

Infectious diseases represent a major world market for pharmaceutical intervention. For several epidemic and endemic viral diseases, vaccines are unavailable and infection is associated with major pathological findings. Some of these important viral targets include the human immunodeficiency virus (HIV), human papilloma virus (HPV), cytomegalovirus (CMV), hepatitis C (hepC) virus, the respiratory syncytial viruses (RSV), and the herpes viruses (including varicella). In many cases, the complete viral genome sequence is known, enabling target genes and biomolecules to be identified and use in the practice of the invention. As will be appreciated, the present invention can identify modulators for many of these targets, and to test these modulators for effective inhibition of virus infectivity. Putative antiviral compounds can be easily evaluated for their effects on viral titer and infectivity in tissue culture or whole animal models of infection.

EXAMPLES

The following examples are provided as a guide for those of ordinary skill in the art, and do not limit the scope of the claimed invention. Except as otherwise specified below, all reagents are used according to the protocols recommended by the manufacturer, and standard or typical culture conditions are employed.

Example 1

Proteases

Like all other retroviruses studied to date, the HIV-1 retrovirus synthesizes a polyprotein which is proteolytically cleaved to yield mature proteins. The Human Immunodeficiency Virus type 1 (HIV-1) protease provides an exemplary proof-of-principle target.

HIV-1 protease has autocatalytic activity (i.e., cleaves itself) which forms the basis for the assay described below. The assay described is easily extended to other retroviruses, and by minor modifications to any protease for which a substrate cleavage site is known. The autocatalytic assay uses a chimeric protein driven from the ADH yeast constitutive promoter (which allows continuous expression of the fusion protein) to transcriptionally activate the expression of a reporter protein ($\beta$) galactosidase gene, or a yeast gene required for cell growth). A yeast strain was used which is deleted for the transcriptional activator GAL4 but contains gene coding for a GAL1-$\beta$ galactosidase fusion protein activated by the GAL4 chimera. Thus, the transcriptional activation of a reporter gene is used as the assay to monitor the activity of the protease.

The fusion protein is encoded by a nuleic acid encoding the HIV protease subcloned between the two functional domains (the Activating and DNA binding domains) of the GAL4 transcriptional activator. In the absence of an inhibitor of the HIV protease, this chimera is, for the most part, unable to act as a viable transcriptional activator due to the autocatalytic activity of the HIV protease/GAL4 construct, which causes the chimera to be cleaved in two, thus separating the required functional domains for transcriptional activation. The HIV protease assay has been previously described in the literature by Murray et al., *Gene*, 134 (1993) 123–128, and for the 3C protease of Coxsackie virus B3 (CVB3) by Das Mahapatra et al. *Proc. Natl. Acad. Sci.* 89 (1992) 4159–4162. One can extend this assay to other retrovirus, e.g. HTLVI and HTLVII, or protease.

Modification of this assay by Smith and Kohorn, *Proc. Nat l Acad. Sci.* 88 (1991) 5159–5162 allows the extension of this assay to those proteases (viral or human) that might not have autocatalytic activity, but for which their substrate cleavage site is known. The modified assay is referred to as the "trans" assay and entails subcloning of the proteolytic cleavage site for a known protease between the two domains of GAL4. In this assay the protease is expressed independently so that it can act in solution to cleave the transcriptional activator in two by binding to its proteolytic cleavage site.

Similar systems can be engineered for the expression of the nine member family of Human CASPASES (involved in apoptosis) and the 19 member family of Human Matrix Metalloproteases (involved in tumor metastasis). Caspase 1 and 3 and MMP-2 are preferred, as are viral proteases from Cytomegalovirus, Herpes-Simplex, Hepatitis C, and Epstein Barr viruses.

As described above, included in the class of proteases is the sub-group of human matrix metalloproteinases (MMPs), which includes certain collagenases and stromelysins. Specific examples are shown in FIG. 8 along with other protease sub-groups(table of proteases).

As a class, MMPs are involved in matrix protein degradation and normal tissue remodeling. The activity of MMPs is also involved in processes in rheumatoid arthritis, tumor invasion, and tumor metastasis, where the activity of MMPs is generally higher than in normal tissue.

Example 2

Channels

This class of proteins mediates nervous and muscular function, signaling events, and ionic balance. The role of this family of proteins in normal physiology is important and involved in a number of diseases from cardiovascular arrhythmia to stroke.

Influenza M2 proton channel: An assay system has been engineered to express the Influenza proton channel M2 in yeast. Kurtz et al., *Antimicrobial Agents and Chemotherapy* (1995) 39: 2204–2209, reported that expression of the Influenza M2 proton channel via the inducible GAL1 promoter in the yeast strain W303 is toxic, and demonstrated the specificity of the toxicity by reversing the phenotype using an inhibitor of the ion channel, amantidine. A number of viral genomes similarly encode ion channels, and the genes encoding such channels can readily be assembled into expression vectors which can be inserted in desired host cells, e.g., yeast, to generate an ARC for use in practicing the methods of this invention. For example, the Vpu and Vpr proteins of human immunodeficiency virus type 1 and NB of influenza B virus likely have ion channel activity (Lamb, *Virology* (1997) 229: 1–11).

$Ca^{2+}$ channels: The assays developed for channels can be further extended by testing the affect of the expression of certain of the subunits (particularly the channel forming beta-subunit(s)) of a number of different voltage-dependent $Ca^{2+}$ channels.

The basis for the $Ca^{2+}$ assay is that expression of a heterologous $Ca^{2+}$ channel in yeast, which raises intracellular $Ca^{2+}$ levels, is toxic because in yeast intracellular $Ca^{2+}$ is deliberately kept low by pumping excess $Ca^{2+}$ into a specialized organelle, the vacuole. If expression of the calcium channel does not increase the $Ca^{2+}$ levels substantially, the calcium sensitivity of the strain can be increased by expressing a toxic calcium-dependent nuclease (high $k_d$) in the cytoplasm. Alternatively, a leader sequence which targets the calcium channel protein to the vacuole can be included in the expression vector from which the protein is expressed. The assay can also be extended to other $Ca^{2+}$ channels, or other ion channels or porins, including splice variants of the beta-subunit from different tissues or transforming the strain with a random cDNA library.

2.2. Complementation Phenotypes $K^+$ channels: This approach differs from growth interference because the assay promotes growth via the ability of a (particularly a human or viral) gene to replace the function of a dysfunctional (mutant) gene. Initial assays in yeast involve a specific yeast strain carrying deletions in the TRK1 and TRK2 genes. This strain cannot grow in low potassium as reported by Ko and Gaber, *Molecular and Cellular Biology* (1991) 11: 4266–4273. The same authors reported the reversal of the growth deficiency by expression of the plant (*Arabidopsis thaliana*) potassium channels KAT1 and KAT2 (Anderson et al., Proc. *Natl Acad Sci,* (1992) 89:3736–40) and the guinea pig cardiac IRK1 gene (Tang et al. *Molecular Biol. Cell* 1995 6: 1231–1240. ARCs coding for the human IRK1 channel, for example, have been constructed, as can other ARCs, for instance, through coding for the known IRK1 genes from different tissue (pituitary gland, pancreas, brain, fetal brain). The assay can also be readily adapted for use with cDNAs encoding proteins involved in cardiac arrhythmia (e.g., KVLQT1, and HERG). Simultaneously, the assays can be even further adapted by transformation with of random cDNA libraries into the trk1, trk2 yeast strain.

A number of representative ion channel sub-groups and ion channels within those subgroups are shown in the table in FIG. 9.

Those skilled in the art will recognized that this invention can be carried out with many variants and modifications, for example using various microbes or cells to provide a surrogate phenotype for many different heterologous genes. As well, a variety of different model systems can be used to indicate the cellular function of a gene product and the therapeutic potential of identified modulators, all within the scope of this invention.

We claim:

1. A method for identifying a modulator of a function of a heterologous biomolecule, comprising:

(a) providing a mixture of host cell populations, each population comprising a different nucleic acid molecule encoding a heterologous biomolecule selected from the group consisting of an RNA and a protein whose function has not been inferred experimentally, wherein the nucleic acid molecule is operatively associated with a promoter, wherein expression of said heterologous biomolecule from said nucleic acid molecule results in a measurable phenotype in each of said host cell populations; and (a) contacting said mixture of host cell populations with a test substance and detecting any changes in a measurable phenotype, wherein a change in a measurable phenotype indicates that said test substance is a potential modulator of said function of said heterologous biomolecule expressed in the host cell population whose measurable phenotype changed following said contacting.

2. The method of claim 1, wherein each host cell population further comprises a nucleic acid tag that distinguishes it from host cell populations that comprise different heterologous biomolecules.

3. The method of claim 1, wherein said mixture of host cell populations is contacted with a plurality of different test substances.

4. The method of claim 3, wherein said mixture of host cell populations is divided into a plurality of aliquots, and different aliquots are contacted with different test substances.

5. The method of claim 1, wherein said phenotype comprises an interference phenotype.

* * * * *